United States Patent [19]

Hägglund

[11] 3,962,395

[45] June 8, 1976

[54] METHOD OF PRODUCING CASTINGS OR OTHER MOULDINGS BY MEANS OF VACUUM SUCTION OF FLEXIBLE CONTAINERS HOLDING GRANULAR MATERIAL

[75] Inventor: Lars Hägglund, Norrkoping, Sweden

[73] Assignee: Landstingens Inkopscentral, Solna, Sweden

[22] Filed: Dec. 4, 1974

[21] Appl. No.: 529,468

Related U.S. Application Data

[63] Continuation-in-part of Ser. No. 310,420, Nov. 29, 1972, abandoned.

[30] Foreign Application Priority Data

Dec. 1, 1971 Sweden.......................... 15404/71

[52] U.S. Cl..................................... 264/91; 264/90; 264/102; 264/220; 264/222
[51] Int. Cl.² ........................................... B29C 1/02
[58] Field of Search ................ 264/109, 91, 92, 90, 264/220, 222, 313, 314, DIG. 30, 223

[56] References Cited
UNITED STATES PATENTS

| | | |
|---|---|---|
| 2,129,240 | 9/1938 | Sanborn.............................. 264/313 |
| 2,326,292 | 8/1943 | Dorman.............................. 285/238 |
| 2,472,754 | 6/1949 | Mead................................. 264/220 |
| 2,613,398 | 10/1952 | Crowell.............................. 264/220 |
| 2,781,273 | 2/1957 | Koch.................................. 264/313 |
| 3,128,322 | 4/1964 | Young ............................... 264/314 |
| 3,823,208 | 7/1974 | Asbelle et al. ...................... 264/222 |

FOREIGN PATENTS OR APPLICATIONS 350,069 3/1922 Germany............................. 285/90

*Primary Examiner*—Willard E. Hoag
*Attorney, Agent, or Firm*—Arthur B. Colvin

[57] ABSTRACT

A method is provided of producing a moulding having a configuration corresponding to the surface configuration of a model. The method comprises the steps of bringing a gas-tight evacuatable container having at least one flexible wall portion in a position relative the configuration of the model such that the wall portion can be deformed to the contours of the model without cracking or creasing. A quantity of granular material is then poured into the container to deform the flexible wall portion to the shape of the model by pressure, whereafter at least a partial vacuum is created in the container to cause the granules to form a solid, persistent mass conforming to the shape of the model. The model is then removed while maintaining the condition of at least partial vacuum in the container.

4 Claims, 7 Drawing Figures

METHOD OF PRODUCING CASTINGS OR OTHER MOULDINGS BY MEANS OF VACUUM SUCTION OF FLEXIBLE CONTAINERS HOLDING GRANULAR MATERIAL

The present application is a continuation-in-part of my pending application Ser. No. 310,420, filed Nov. 29, 1972 now abandoned.

The present invention concerns a method of producing a moulding with a contour which corresponds to an outer and/or inner contour of a model. In this connection the moulding can be either an end product or a part-product, such as a casting intended for subsequent production of an end product such as the product cast in the casting.

The model, in its turn, may be e.g. the object (pattern) which is to be used for producing a mould in or around which an article is to be produced by casting, but the model may also be a part, from which it is desired to obtain a good impression, i.e. a negative, which in turn is to be used for producing a positive with the same surface form as the said part.

One type of moulding for the production of which the invention should be particularly suitable covers various orthopaedic products, such as mould for making above-knee prostheses, lasts for orthopaedic shoes, foot sockets etc.

The problem basic to the invention consists in obtaining an improved type of process by means of which moulding such as various types of casting can be produced with great accuracy and at lower cost than hitherto.

Where orthopaedic products are concerned, the purpose in particular is to obtain a method which is appreciably simpler than the methods hitherto used, where the end products envisaged could only be produced with very great difficulty, and often gave a bad fit. The method according to the invention shall also enable appreciably faster production of the moulding in question than has hitherto been possible.

The present invention comprises the steps of: providing a gas-tight evacuable container of variable volume, said container including a conduit leading to the interior thereof and at least one, readily deformable, flexible and extendible wall portion adapted to be conformed to said contour; placing said wall portion of said container against the surface portion sought to be reproduced, to cause said wall to be partially deformed to the contours of said surface; introducing into the interior of said container, through said conduit, a quantity of granular material, thereby to cause said wall to be further deformed and conform closely to the contours of said surface; evacuating through said conduit at least a part of the fluid within said container to create a negative pressure (vacuum) within said container whereby said granular material is caused to stiffen into a persistent shape and said wall conforms to said contour; removing said wall from contact with said surface while maintaining said negative pressure in said container whereby said deformed wall surface defines an accessible mould component.

Such methods have inter alia been described in U.S. Patent Nos. 2,488,922 (Mead), 2,472,754 (Mead) and 2,499,324 (Mead).

One primary version of said method is characterized by using as a model a previously vacuum-sucked first gas-tight container enclosing granular material and having a deformable, flexible and extensible wall, part of which encloses no part of the granular material inside said container, and by using the last-mentioned wall part as a flexible wall means for a second container which is then vacuum-sucked by using the same method as used when vacuum-sucking said first container. This method is preferably executed by using an elastic hose as a flexible wall portion for both a model in the form of an outer (negative) mould having an inflexible wall portion and being produced by vacuum-sucking a first container, as well as for an inner (positive) mould provided with vacuum-creating means, wherein a first annular portion of the hose is attached to the inflexible model wall portion and a second annular portion of the hose is attached to said vacuum-creating means, and thereafter evacuating said inner mould.

The last-mentioned version of the method may be used for transferring the configuration of a negative (outer) mould into a positive (inner) mould or vice versa. This is achieved by using a flexible wall means comprising a wall portion of the outer mould as well as of the inner mould.

When using a container comprising an annularly closed inflexible model wall, a doubly folded annular portion of the hose can be attached to the inflexible model wall portion, and an annular free edge portion of the hose be attached to the vacuum-creating means.

By first adding granular material to the free surface of a previously vacuum-sucked mould in a first container, and by applying firmly on the new container thus obtained followed by vacuum-suction of the new container and removal of the granular material from the first container, the new container will have the same surface configuration as the original (first) one, but with the configuration applied on the reverse side of the flexible wall portion.

An interesting application of this method is the production of a mould with negative clearance to a model both outside and inside.

Examples of the invention as defined above will be described below.

Another primary version of the new method according to the present invention is characterized by placing, before filling the container with granular material and vacuum-sucking same, a compressible porous and yieldable material on the granular material side of part of the flexible wall portion to be conformed to the model surface, thereby to introduce a predictable clearance space between said part of said wall portion and said surface when the container is vacuum-sucked (evacuated).

By means of this method it is possible to obtain a moulding having a configuration surface part of which is situated at a desired distance from the surface of the model to be reproduced.

The porous and yieldable material (e.g. cellular plastics), which is compressible with vacuum, is applied on the wall portion of the mould in the region where a space outside the model is required and with a thickness which is a function of both the compressibility of the material due to the later applied vacuum, and the desired space. A quantity of granular material is poured into the mould which takes a shape due to the compressible material, whereafter at least a partial vacuum is created in the mould to cause the granules to form a solid mass.

When the vacuum suction is increased, the flexible wall portion will be pressed against the compressible material which is then pressed against the solid granular material whereby the required space is created between the flexible wall portion and the model surface.

The present invention will now be described with reference to the attached drawings in which some examples or embodiments of the method are illustrated.

Figure 6:
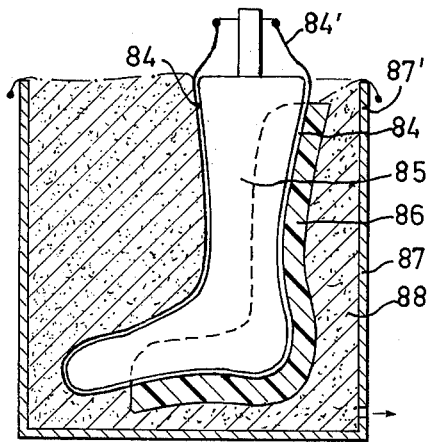
Figure 7:
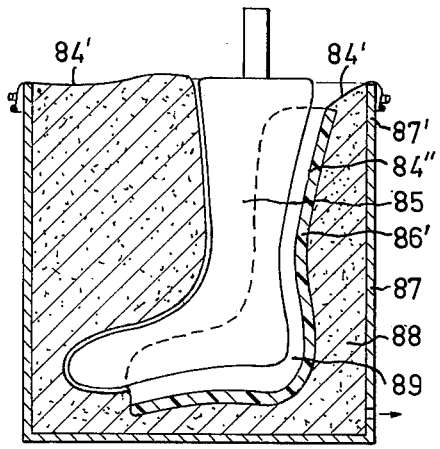

and FIGS. 6 and 7 show in vertical sections, an example of the making of a foot socket.

Figure 1:
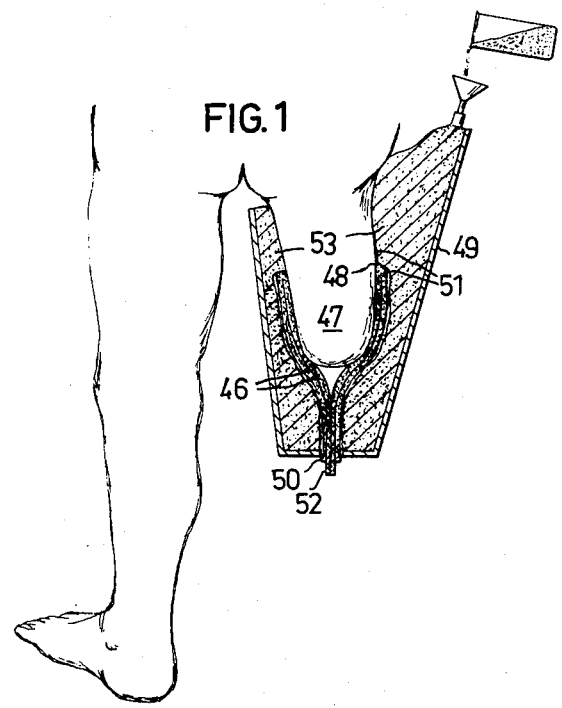
FIG. 1 shows, in vertical section, an arrangement for producing a stump negative for above-knee prostheses.

The method according to the invention can with advantage be used for producing above-knee prosthesis sockets, and here, in order to get a good fit of the socket to the stump, the stump should be extended before casting. FIG. 1 shows the production of an above-knee prosthesis socket. A sock 46, turned in on itself, e.g. an open glass-fibre tricot sock, is here drawn round the stump 47 with the folded edge of the sock, 48, upwards, before the stump is lowered into the mould arrangement 49, which in this case has an opening 50 in the bottom and which it is convenient to have all in one piece, and which, if necessary, has a flexible window in the outer shell so that the annular sand moulding, when vacuum is being applied, will not become noticeably greater than the stump. To get the rubber sheeting 51 to conform continuously to the outstretched stump, the inner part 52 of the sock is drawn out through the bottom opening 50 in the mould arrangement; the sand 53 forces the rubber sheeting against the stump and fills up the space appearing momentarily at the place where the edge 48 of the sock has just been.

Figure 2:
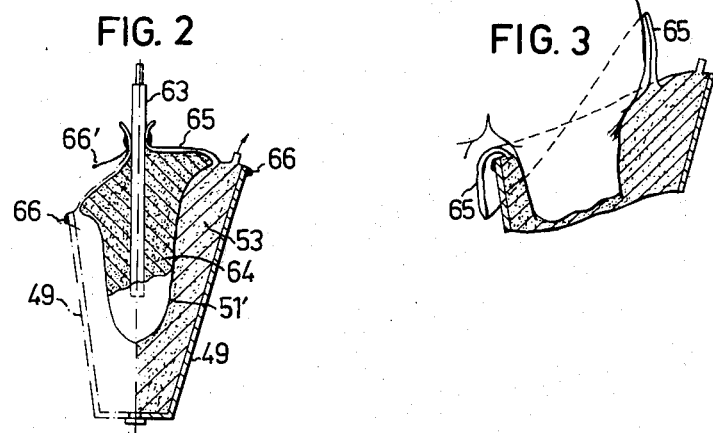
FIG. 2 shows, in vertical section, how a positive moulding is produced from the stump negative of FIG. 1.
Figure 3:
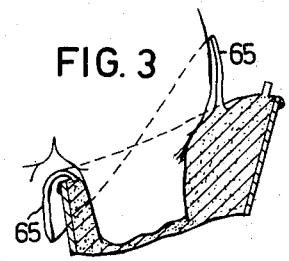
FIG. 3 shows, in vertical section, the upper portion of the rubber foil used with the arrangement of FIG. 2.

FIG. 2 illustrates how the negative mould 51', 53 can be readily converted to a positive mould, by inserting a vacuum suction pipe 63 into the cavity of the amputation stump 47 (FIGS. 1 and 3) and pouring sand 64 into the cavity, whereafter the doubly folded vacuum edge portion 65 of the rubber foil 51' (FIGS. 2 and 3) is drawn together and sealed around the pipe 63, so that air can be removed by suction from the sand 64 in a normal manner, to create a vacuum. The sand positive thus produced is then removed from the mould arrangement 49, by releasing the edge 66 of the rubber foil 51' from the upper edge of the arrangement. For the sake of simplicity, the right half of FIG. 2 shows the situation when air has been withdrawn from the body of sand 64 to cause a vacuum therein, while the left half of the Figure shows the situation when the mould arrangement 49 has been removed, the edge 66 having sprung back to position 66'.

Figure 4:
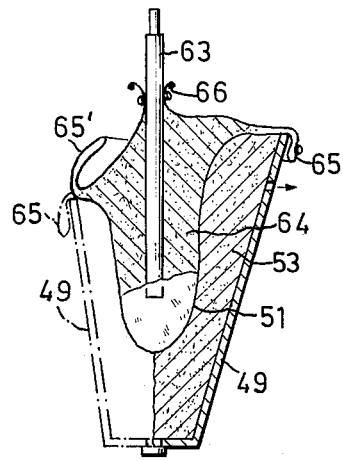
FIG. 4 shows, in vertical section, an embodiment similar to the one shown in FIG. 2.

FIG. 4 illustrates how a negative mould 51, 53, in this case corresponding to an above-knee amputation stump, can readily be converted into a positive mould by inserting a vacuum suction pipe 63, into the cavity of the amputation stump 47 and pouring sand 64 into the cavity, whereafter the free edge 166 of the rubber foil 51 is drawn together and sealed around the pipe 63, so that air can be removed by suction from the sand 64 in a normal manner, to create a vacuum. The sand positive thus produced is then removed from the mould arrangement 49 by releasing the doubly folded edge portion 165 of the rubber foil 51 from the upper edge of the arrangement 49. For the sake of simplicity, the right half of FIG. 4 shows the situation when air has been withdrawn from the body of sand 64 to cause a vacuum therein, while the left half of FIG. 4 shows the situation when the mould arrangement 49 has been removed, the edge portion 165 having sprung back to position 165'. On the positive mould of the stump thus obtained, a plastic socket is formed, which is required for the production of a leg prosthesis.

Figure 5:
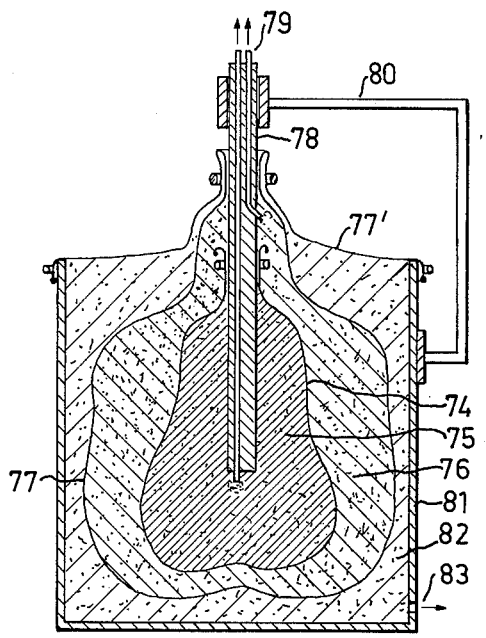
FIG. 5 shows, in vertical section, an embodiment of an arrangement used for making a glass vase.

FIG. 5 shows an example of production of a mould having negative clearance both outside and inside and having no partition.

Configuration 74 consists of an elastic film, for example of rubber or heat-formed plastic foil, which maintains its shape with the aid of the vacuum-sucked granular material 75 inside the film. The outer configuration is obtained by inserting additional granular material outside the foil 74 but inside the elastic foil 77, sealing the container against the evacuation pipe 78, connecting the container to reduced vacuum 79, forming the foil 77 to desired configuration and applying complete vacuum suction on container 76.

The unit thus obtained using suction pipe 78 and two rigid moulds 75, 74 and 76, 77 within each other, is thereafter fixed by means of the suction pipe which is firmly connected by means 80 to container 81 which is then filled with granular material 82, sealed with part of the outer foil 77' and vacuum-sucked via conduit 83.

By releasing the sealing of this foil 77 to the suction pipe and removing the granular material 76 inside, for example by emptying, blowing off or rinsing, a mould is obtained in which it is possible to mould plastics, glass, metals or other suitable material.

When such a material mass has hardened, the previously vacuum-sucked containers are ventilated whereafter the moulded piece is uncovered.

The example referred to above is intended for production of a glass vase with the inner surface shaped as a "pear" and the other surface formed as an "apple", but the method can naturally be applied within a variety of areas, for example moulding of footbeds or soles for orthopaedic shoeware, moulding of plastics or metal objects, with vacuum-suction applied, both as an outer mould as well as in the form of a core, for moulding of sanitary-ware with inner spaces, as well as added moulding of foam plastics in a variety of layer thicknesses and with negative clearances and without joints on different objects, among others furniture bases.

When a foot socket is being made, which as is known consists of a shell, wadded in places, round the sole and heel parts of the foot and shin, first a negative mould of the modelled sand-vacuum positive is produced. Thermoplast is poured into the space (delimited by double adhesive tape) which forms between the positive and the negative when the sand in the outer mould is compressed under vacuum. In the places where extra thick layers are required, on the sand side of the rubber surface of the outer mould a cellular plastics or foamed rubber layer is then fixed which has the property of compressing more than the sand does when under vacuum, and thus causing an increase in the space between the positive and the negative.

When a foot socket is being made (see FIG. 6), a latex rubber hose 84 (or elastic plastic foil) is first drawn over the positive model 85, which for example may consist of a rubber socket with vacuum-sucked sand which has been formed as a foot or of insulated plaster of Paris. A layer of cellular plastics 86, or other relatively easily compressible material is then applied on the rubber hose, on the area where the foot socket shall be moulded, and with a thickness which to some extent exceeds the thickness required on the foot socket.

When the prepared unit has been put into a container 87, sand 88 is poured into same, the upper part 84' of the rubber hose is folded over and sealed against the upper edge 87' of the container (FIG. 7) and vacuum suction is applied on the container. The sand 88 hardens now first of all without any change of position, and thereafter the rubber hose 84 is pulled in towards sand 88, the cellular plastics 86' being pressed together and a space 89 is obtained between model 85 and the new hose contour 84'', in which space plastics is moulded. After hardening the container is vented and the moulded and finished foot socket is removed.

The straps, buckles or other details which may be required, partly or completely moulded into the goods, should from the beginning be attached between the model and the rubber socket, for example by means of double-adhesive tape. Various layers, with thicknesses independent of each other, can be produced lying on top of each other according to the method described above, for example to obtain a soft inner lining in various parts of the foot socket.

In some cases, for example where a space is required outside of a complete outer configuration, it is necessary to fix the model in position in relation to the container in order to obtain the required space. The method described can of course be used for a large number of purposes, for example to produce shoeware for rheumatic patients, gloves, soft or firm inner or outer linings or covers, for example furniture, plastic-, glassware or cast metal goods with negative clearances without divisions and with a variety of thicknesses in different areas, as well as vacuum-sucked sockets, tubings or cloth consisting of vacuum-sucked granular material encased in flexible walls, obtained by filling the granular material in the middle space according to the method described with vacuum suction applied.

What I claim is:

1. In a method of making a contoured mold member corresponding in shape to contours of a model, the steps comprising:
    a. forming a first air-tight chamber by sealing a readily deformable, flexible and extensible member about a peripheral edge of a container wall, said member including a portion extending beyond confines of said container;
    b. placing a model, contours of which are to be reproduced, against said extensible member and causing said extensible member to be partially conformed to said contours;
    c. introducing granular material into said chamber through a conduit thereto and causing said member to be conformed further to said contours;
    d. evacuating fluid at least partially from said first chamber creating a partial vacuum therein and causing said granular material to stiffen into a persistent shape and causing said extensible member to conform further to said contours;
    e. while maintaining said partial vacuum removing said model from contact with said extensible member thereby exposing a surface of said extensible member conformed to said contours of said model, said surface defining a mold cavity;
    f. filling said cavity with other granular material;
    g. sealing portions of said member, extending beyond confines of said container, to form a second airtight chamber about said other granular material; and
    h. evacuating fluid from said second chamber to form a positive mold member from said other granular material and said extensible member.

2. The method of claim 1, wherein a compressible porous sheet material is placed adjacent said extensible member on a side opoosite said model before evacuating said fluid from said first container and said evacuating from said first container compresses said material.

3. The method in accordance with claim 1 wherein said first annular wall portions of said hose are double folded and air is evacuated from said first container through free edge portions of said hose adjacent said double folded portion.

4. The method of claim 1, wherein said extensible member is an elastic hose, sealing contact between said hose and said first container is effected by engagement between said container wall and a first annular portion of said hose, and said mold cavity is sealed by sealing second annular portions of said hose extending beyond said confines of said first container.

* * * * *